(12) United States Patent
Deguchi et al.

(10) Patent No.: US 11,463,668 B2
(45) Date of Patent: Oct. 4, 2022

(54) MEDICAL IMAGE PROCESSING DEVICE, MEDICAL OBSERVATION SYSTEM, AND IMAGE PROCESSING METHOD

(71) Applicant: Sony Olympus Medical Solutions Inc., Tokyo (JP)

(72) Inventors: Tatsuya Deguchi, Tokyo (JP); Satoshi Mitsui, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 10 days.

(21) Appl. No.: 17/134,529

(22) Filed: Dec. 28, 2020

(65) Prior Publication Data

US 2021/0266508 A1     Aug. 26, 2021

(30) Foreign Application Priority Data

Feb. 21, 2020   (JP) .............................. JP2020-028830

(51) Int. Cl.

| *A61B 1/04* | (2006.01) |
|---|---|
| *A61B 1/06* | (2006.01) |
| *H04N 9/77* | (2006.01) |
| *H04N 5/225* | (2006.01) |
| *A61B 1/00* | (2006.01) |

(52) U.S. Cl.
CPC ........... *H04N 9/77* (2013.01); *A61B 1/00009* (2013.01); *A61B 1/043* (2013.01); *A61B 1/0653* (2013.01); *H04N 5/2256* (2013.01); *A61B 1/0005* (2013.01); *H04N 2005/2255* (2013.01)

(58) Field of Classification Search
CPC ... A61B 1/043; A61B 1/00009; A61B 1/0005; A61B 1/0638; A61B 1/0661
See application file for complete search history.

(56) References Cited

U.S. PATENT DOCUMENTS

| 2008/0239070 | A1* | 10/2008 | Westwick | ............ A61B 1/0684 348/E5.029 |
|---|---|---|---|---|
| 2013/0096376 | A1* | 4/2013 | Takei | .................. H04N 5/2356 600/103 |
| 2014/0301617 | A1* | 10/2014 | Shida | ................. A61B 1/00009 382/128 |
| 2016/0007856 | A1* | 1/2016 | Ishihara | ............. G02B 23/2469 600/476 |
| 2020/0402208 | A1* | 12/2020 | Talbert | .................... G06T 7/521 |
| 2020/0404151 | A1* | 12/2020 | Talbert | ................. A61B 1/0638 |
| 2020/0404171 | A1* | 12/2020 | Talbert | ................. A61B 1/0638 |

* cited by examiner

*Primary Examiner* — Fabio S Lima

(74) *Attorney, Agent, or Firm* — Xsensus LLP

(57) ABSTRACT

A medical image processing device includes an image processor configured to: generate an output image by combining a first captured image obtained by capturing light from an observation target irradiated with light in a first wavelength band and a second captured image obtained by capturing fluorescence from the observation target irradiated with excitation light, with corresponding pixels; output a brightness signal value of a target pixel to be generated in the output image, as either a brightness signal value of a first corresponding pixel corresponding to the target pixel in the first captured image or a brightness signal value of a second corresponding pixel corresponding to the target pixel in the second captured image; and output a color difference signal value of the target pixel in the output image as a value generated by using the brightness signal value of the second corresponding pixel.

15 Claims, 11 Drawing Sheets

MEDICAL IMAGE PROCESSING DEVICE, MEDICAL OBSERVATION SYSTEM, AND IMAGE PROCESSING METHOD

CROSS-REFERENCE TO RELATED APPLICATION

This application claims priority from Japanese Application No. 2020-028830, filed on Feb. 21, 2020, the contents of which are incorporated by reference herein in its entirety.

BACKGROUND

The present disclosure relates to a medical image processing device, a medical observation system, and an image processing method.

In recent years, in endoscopes, an observation method for observing special light with special light has been devised in addition to white light. Specifically, examples of special light observation include a technique called narrow band imaging (NBI), a technique called infra-red imaging (IRI), a technique called auto fluorescence imaging (AFI), a technique called photodynamic diagnosis (PDD), and the like.

For example, in the IRI, a substance called indocyanine green (ICG), which has an absorption peak in near-infrared light with a wavelength of about 805 nm in blood, is intravenously injected as a contrast agent, excitation light with a wavelength of about 750 to 810 nm is irradiated to observe a shadow of a blood vessel part of a submucous layer due to absorption of ICG from a fluorescence image in which fluorescence of about 840 nm is detected, and a running state of blood vessels and lymph vessels is diagnosed.

In addition, in auto fluorescence observation in special light observation, there is known a technique for observing an observed region or a state of a lesion of a subject while switching between a normal light observation mode in which normal light observation is performed and an auto fluorescence observation mode in which auto fluorescence observation is performed (for example, see JP 2013-102899 A). In such a technique, a composite image obtained by combining a normal light image captured by irradiating the normal light and a fluorescent image captured by the auto fluorescence by irradiating the excitation light, is displayed on a display device. The composition of the normal light image and the fluorescence image is displayed in pseudo color on the display device by assigning an image signal of the fluorescent image to a G channel of the composite image and assigning image signals of an R channel and a B channel of the normal light image to an R channel and a B channel of the composite image.

SUMMARY

In JP 2013-102899 A described above, since the image signal of the auto fluorescent image, which is a special light observation image, is assigned to the G channel of the composite image, combined with the normal light image, and displayed in the pseudo color, there is a problem that the details in the lesion part of a living tissue disappear.

There is a need for a medical image processing device, a medical observation system, and an image processing method that are able to generate an appropriately observable image even when the normal white light and the special light observation image are combined.

According to one aspect of the present disclosure, there is provided a medical image processing device including an image processor configured to: generate an output image by combining a first captured image obtained by capturing light from an observation target irradiated with light in a first wavelength band and a second captured image obtained by capturing fluorescence from the observation target irradiated with excitation light, with corresponding pixels, the first captured image being an observation target that emits the fluorescence when irradiated with the excitation light in a second wavelength band that is different from the light in the first wavelength band and being input from the outside, and the second captured image being input from the outside; output a brightness signal value of a target pixel to be generated in the output image, as either a brightness signal value of a first corresponding pixel corresponding to the target pixel in the first captured image or a brightness signal value of a second corresponding pixel corresponding to the target pixel in the second captured image; and output a color difference signal value of the target pixel in the output image as a value generated by using the brightness signal value of the second corresponding pixel.

DETAILED DESCRIPTION

Figure 1:
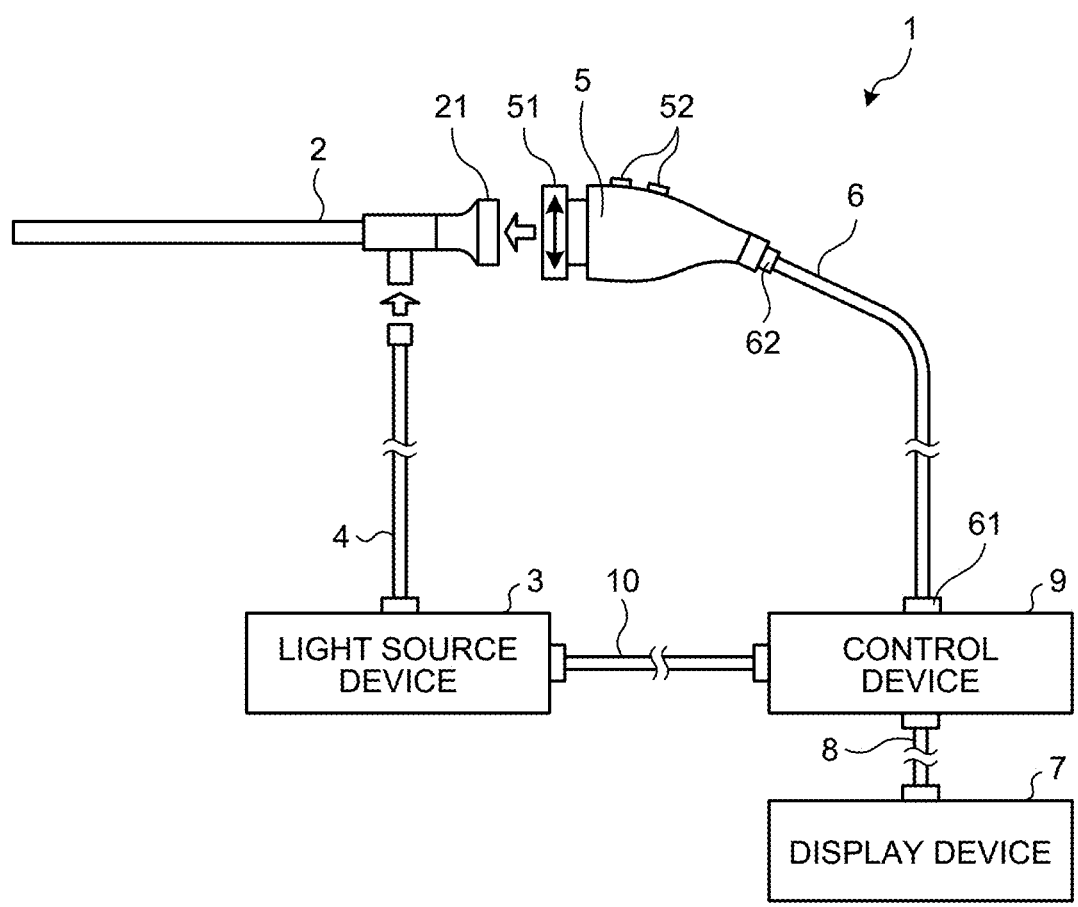
FIG. 1 is a diagram illustrating a schematic configuration of an endoscope system according to a first embodiment.

Hereinafter, modes for carrying out the present disclosure will be described in detail with reference to the drawings. Note that the present disclosure is not limited by the following embodiments. In addition, each of the figures referred to in the following description merely schematically illustrates the shape, size, and positional relationship to the extent that the contents of the present disclosure may be understood. That is, the present disclosure is not limited to the shape, size, and positional relationship exemplified in each figure. Further, in the description of the drawings, the same parts will be described with the same reference numerals. Furthermore, as an example of a medical observation system according to the present disclosure, an endoscope system including a rigid endoscope will be described.

First Embodiment

Outline Configuration of Endoscope System

FIG. 1 is a diagram illustrating a schematic configuration of an endoscope system according to a first embodiment. An endoscope system 1 illustrated in FIG. 1 is used in a medical field and a system that is inserted into a living body of a subject such as a living body of a human or an animal and observes the subject by displaying an image obtained by capturing the inside of the living body. Note that in the first embodiment, as the endoscope system 1, a rigid endoscope system using a rigid endoscope (insertion portion 2) illustrated in FIG. 1 will be described, but the present disclosure is not limited thereto, and for example, a flexible endoscope system may be used.

The endoscope system 1 illustrated in FIG. 1 includes an insertion portion 2, a light source device 3, a light guide 4, a camera head 5 (endoscope imaging device), a first transmission cable 6, a display device 7, a second transmission cable 8, a control device 9, and a third transmission cable 10.

The insertion portion 2 has an elongated shape that is hard or at least partially soft. The insertion portion 2 is inserted into a subject such as a patient. The insertion portion 2 has an optical system that is configured with one or a plurality of lenses and combines observation images provided therein.

One end of the light guide 4 is connected to the light source device 3. Under the control of the control device 9, the light source device 3 emits (supplies) white light for illuminating the inside of the subject to one end of the light guide 4, and excitation light or infrared light to a substance administered or sprayed to the subject. The light source device 3 is configured by using a semiconductor laser element such as a light emitting diode (LED) light source or a laser diode (LD). As illustrated in FIG. 1, the light source device 3 and the control device 9 may be configured to communicate individually or may be integrated.

One end of the light guide 4 is detachably connected to the light source device 3, and the other end thereof is detachably connected to the insertion portion 2. The light guide 4 guides a light emitted from the light source device 3 from one end to the other end and supplies the light to the insertion portion 2.

An eyepiece 21 of the insertion portion 2 is detachably connected to the camera head 5. Under the control of the control device 9, the camera head 5 generates image data (imaging signal) by capturing an observation image formed by the insertion portion 2, and outputs the image data. In addition, the camera head 5 includes an operation ring portion 51 rotatably provided in a circumferential direction, and a plurality of input portions 52 that receive inputs of instruction signals instructing various operations of the endoscope system 1.

One end of the first transmission cable 6 is detachably connected to the control device 9 via a first connector portion 61, and the other end thereof is connected to the camera head 5 via a second connector portion 62. The first transmission cable 6 transmits the image data output from the camera head 5 to the control device 9, and transmits a control signal, a synchronization signal, a clock signal, a power, and the like output from the control device 9 to the camera head 5.

The display device 7 may be connected to the control device 9 via the second transmission cable 8, and displays a display image based on the image data processed by the control device 9 under the control of the control device 9.

One end of the second transmission cable 8 is detachably connected to the display device 7, and the other end thereof is detachably connected to the control device 9. The second transmission cable 8 transmits the display image based on the image data processed by the control device 9 to the display device 7.

The control device 9 is realized by using a memory, and a processor having hardware such as a central processing unit (CPU), a graphics processing unit (GPU), an application specific integrated circuit (ASIC), and a field programmable gate array (FPGA). The control device 9 comprehensively controls operations of the light source device 3, the camera head 5, and the display device 7 through each of the first transmission cable 6, the second transmission cable 8, and the third transmission cable 10 according to a program recorded in the memory. In addition, the control device 9 performs various image processing on the image data input from the camera head 5 via the first transmission cable 6 and outputs the image-processed image data to the second transmission cable 8.

One end of the third transmission cable 10 is detachably connected to the light source device 3, and the other end thereof is detachably connected to the control device 9. The third transmission cable 10 transmits the control signal from the control device 9 to the light source device 3.

Detailed Configuration of Light Source Device, Camera Head, and Control Device

Figure 2:
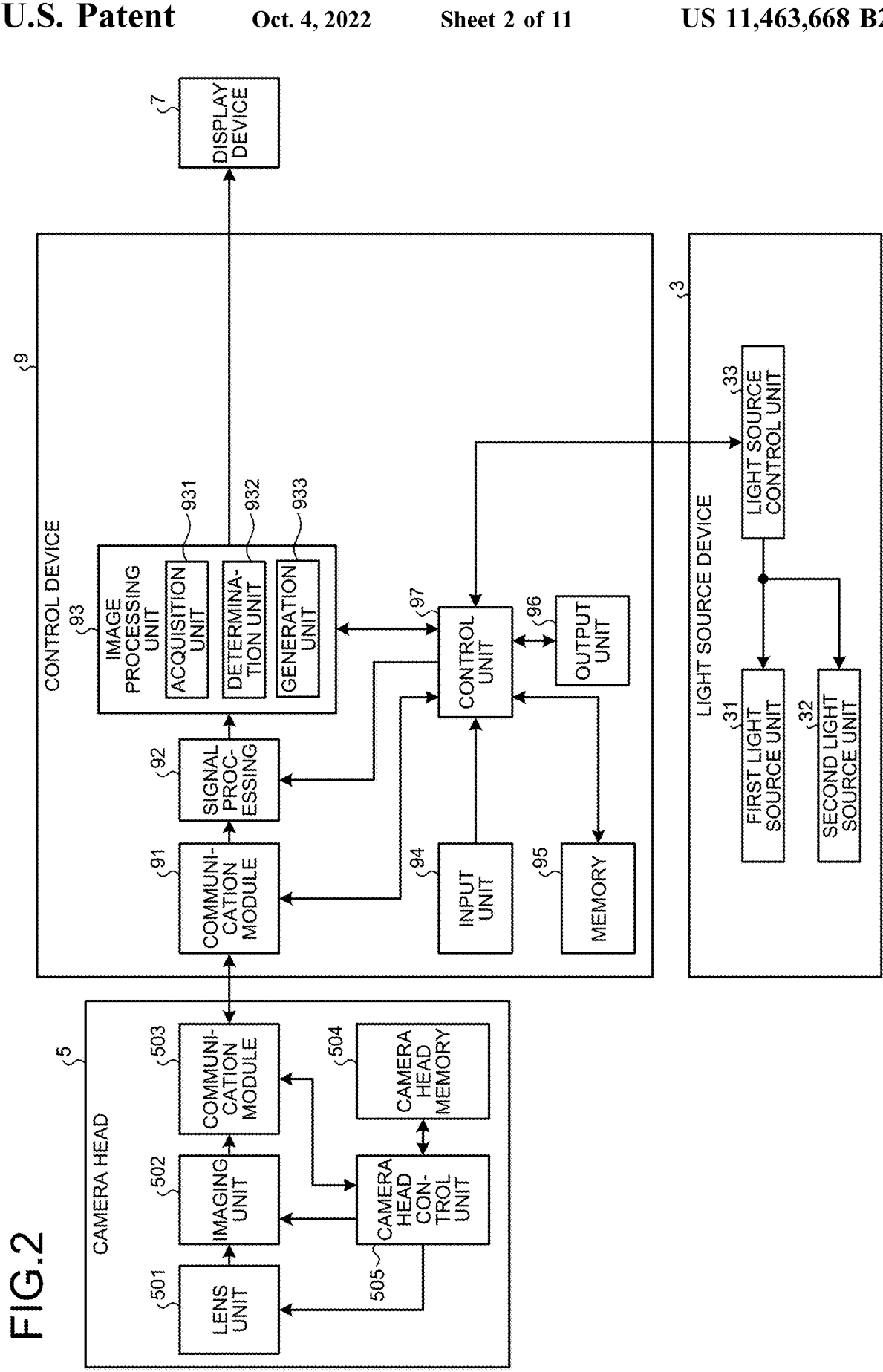
FIG. 2 is a block diagram illustrating a functional configuration of a light source device, a camera head, and a control device included in the endoscope system according to the first embodiment.

Next, a functional configuration of the light source device 3, the camera head 5, and the control device 9 will be described. FIG. 2 is a block diagram illustrating a functional configuration of the light source device 3, the camera head 5, and the control device 9 included in the endoscope system 1. In FIG. 2, for convenience of explanation, the insertion portion 2, the light guide 4, the first transmission cable 6, the second transmission cable 8, and the third transmission cable 10 are omitted.

Configuration of Light Source Device

First, a configuration of the light source device 3 will be described.

The light source device 3 includes a first light source unit 31, a second light source unit 32, and a light source control unit 33.

Under the control of the light source control unit 33, the first light source unit 31 supplies the white light to be irradiated to the subject to the insertion portion 2 by pulse-emitting the white light which is normal observation light. The first light source unit 31 is realized by using a red semiconductor laser element capable of irradiating red (wavelength band 600 nm to 700 nm) light, a blue semiconductor laser element capable of irradiating blue (wavelength band 400 nm to 500 nm) light, and a green semiconductor laser element capable of irradiating green (wavelength band 500 nm to 600 nm) light. Note that the first light source unit 31 is configured by using the red, blue, and green semiconductor laser elements, but is not limited thereto, and may use a white semiconductor laser element capable of irradiating white light. In addition, the first light source unit 31 does not have to be a semiconductor laser element, and may be, for example, a light emitting diode (LED) or the like. In addition, the first light source unit 31 is not limited to a simultaneous lighting that simultaneously irradiates each of the red, green, and blue lights, but may be a surface-sequence system that sequentially irradiates each of the red, green, and blue lights.

Under the control of the light source control unit 33, the second light source unit 32 pulse-emits near-infrared light, which is one of the special lights irradiated to the subject via the insertion portion 2. Specifically, under the control of the light source control unit 33, the second light source unit 32 emits infrared light (wavelength band 700 to 1000 nm) that excites the substance (fluorescent substance) injected into the subject, and supplies the emitted infrared light to the insertion portion 2. Specifically, the second light source unit 32 emits near-infrared light including 790 nm to 820 nm (center wavelength of 805 nm) and 905 nm to 970 nm (center wavelength of 940 nm) as excitation light. The second light source unit 32 is configured by using a semiconductor laser element capable of irradiating a fluorescent substance with excitation light, a filter that transmits only a predetermined wavelength band, and the like. Here, the fluorescent substance is indocyanine green. The indocyanine green has an absorption peak of near infrared light having a wavelength of about 805 nm in the blood, is intravenously injected into the subject as a contrast agent, and emits fluorescence of about 840 nm.

The light source control unit 33 controls the light emission of the first light source unit 31 and the second light source unit 32 under the control of the control device 9. The light source control unit 33 is realized by using a memory, and a processor having hardware such as a CPU, an ASIC, and an FPGA.

Configuration of Camera Head

Next, a configuration of the camera head 5 will be described.

The camera head 5 includes a lens unit 501, an imaging unit 502, a communication module 503, a camera head memory 504, and a camera head control unit 505.

The lens unit 501 is configured by using one or a plurality of lenses, and forms a subject image on a light receiving surface of the imaging unit 502. In addition, under the control of the camera head control unit 505, the lens unit 501 performs auto focus (AF) that changes a focal position and optical zoom that changes a focal length by moving a lens along an optical axis direction by a driving unit (not illustrated). Note that in the first embodiment, the lens unit 501 may be provided with a diaphragm mechanism and a detachable optical filter mechanism for cutting infrared light reflected from the subject on the optical axis.

Under the control of the camera head control unit 505, the imaging unit 502 (image sensor) generates a captured image based on image data (RAW data) by receiving a subject image imaged by the insertion portion 2 and the lens unit 501 and performing photoelectric conversion, and outputs the captured image to the communication module 503. Specifically, the imaging unit 502 outputs a first captured image (hereinafter, simply referred to as "first captured image") to the communication module 503 based on first captured image data generated by capturing the light reflected from an observation target by irradiating the observation target to which the substance is administered to the subject with white light, which is light in a first wavelength band, by the first light source unit 31. In addition, in a special light observation mode, the imaging unit 502 outputs a second captured image (hereinafter, simply referred to as "second captured image") to the communication module 503 based on the second captured image data generated by capturing a fluorescence from the observation target by irradiating the observation target to which the substance is administered to the subject with near-infrared light, which is light in a second wavelength band different from the light in the first wavelength band, by the second light source unit 32. Here, the second captured image emphasizes a specific region in substantially the same observation field of view as the first captured image. Further, the specific region is a region in which a substance containing a fluorescent substance, for example, ICG, is administered to the observation target of the subject. The imaging unit 502 is configured by using a charge coupled device (CCD), a complementary metal oxide semiconductor (CMOS), and the like.

The communication module 503 outputs various signals transmitted from the control device 9 via the first transmission cable 6 to each unit in the camera head 5. In addition, the communication module 503 performs parallel-serial conversion processing on information on the first image and the second image generated by the imaging unit 502, a current state of the camera head 5, and the like via the first transmission cable 6, and outputs a processing result to the control device 9.

The camera head memory 504 stores camera head information for identifying the camera head 5 and various programs executed by the camera head 5. Here, the camera head information includes the number of pixels of the imaging unit 502, a pixel pitch, identification (ID) of the camera head 5, and the like. The camera head memory 504 is configured by using a volatile memory, a non-volatile memory, and the like.

The camera head control unit 505 controls the operation of each unit constituting the camera head 5 based on various signals input from the communication module 503. The camera head control unit 505 is configured by using a processor having a memory and hardware such as a CPU.

Configuration of Control Device

Next, a configuration of the control device 9 will be described.

The control device 9 includes a communication module 91, a signal processing unit 92, an image processing unit 93, an input unit 94, a memory 95, an output unit 96, and a control unit 97.

The communication module 91 outputs various signals including the first captured image, the second captured image, and the like input from the camera head 5 to the control unit 97 or the signal processing unit 92. In addition, the communication module 91 transmits various signals input from the control unit 97 to the camera head 5. Specifically, the communication module 91 performs parallel-serial conversion processing or the like on the signal input from the control unit 97 and outputs the processed signal to the camera head 5. Further, the communication module 91 performs serial-parallel conversion processing or the like on the signal input from the camera head 5 and outputs the processed signal to each unit constituting the control device 9.

The signal processing unit 92 performs signal processing such as noise reduction processing or A/D conversion processing on the first captured image or the second captured image input from the camera head 5 via the communication module 91 and outputs the processed captured image to the image processing unit 93.

Under the control of the control unit 97, the image processing unit 93 performs various image processing on the first captured image or the second captured image input from the signal processing unit 92 and outputs the processed captured image to the display device 7. Here, as predetermined image processing, there is various known image processing such as demosaic processing, color space conversion processing, color correction processing, color enhancement processing, and contour enhancement processing. The image processing unit 93 is configured by using a memory and a processor having hardware such as a GPU, an FPGA, or a CPU. In addition, the image processing unit 93 generates an output image by combining the first captured image and the second captured image with the corresponding pixels, and outputs the output image to the display device 7. Specifically, the image processing unit 93 outputs a brightness signal value of the target pixel to be generated in the output image as either a brightness signal value of a first corresponding pixel corresponding to a target pixel in the first captured image or a brightness signal value of a second corresponding pixel corresponding to a target pixel in the second captured image, and outputs a color difference signal value of the target pixel in the output image as a value generated by using a brightness signal value of a second corresponding pixel. The image processing unit 93 includes an acquisition unit 931, a determination unit 932, and a generation unit 933. Note that in the first embodiment, the image processing unit 93 functions as a medical image processing device.

The acquisition unit 931 acquires the first captured image and the second captured image from the camera head 5 via the communication module 91 and the signal processing unit 92.

The determination unit 932 determines whether or not the brightness signal value of the second corresponding pixel corresponding to the target pixel in the second captured image is a predetermined threshold value or more. Here, the threshold value is a value at a level that is not affected by black noise.

The generation unit 933 generates an output image by combining the first captured image and the second captured image acquired by the acquisition unit 931 with the corresponding pixels, and outputs the output image to the display device 7. Specifically, the generation unit 933 outputs a brightness signal value of the target pixel to be generated in the output image as either a brightness signal value of a first corresponding pixel corresponding to a target pixel in the first captured image or a brightness signal value of a second corresponding pixel corresponding to a target pixel in the second captured image, and outputs a color difference signal value of the target pixel in the output image as a value generated by using a brightness signal value of a second corresponding pixel. In addition, when a vector is defined by two coefficients a and b for a preset pseudo color in a two-dimensional color space, the generation unit 933 outputs a Cb value and a Cr value, which are the color difference signal values of the target pixel in the output image, as a value generated by multiplying the brightness signal value of the second corresponding pixel corresponding to the target pixel in the second captured image by the coefficient a, and a value generated by multiplying the brightness signal value of the second corresponding pixel corresponding to the target pixel in the second captured image by the coefficient b. Further, when the determination unit 932 determines that the brightness signal value of the second corresponding pixel corresponding to the target pixel in the second captured image is a predetermined threshold value or more, the generation unit 933 outputs the brightness signal value of the target pixel to be generated in the output image as the brightness signal value of the second corresponding pixel corresponding to the target pixel in the second captured image. In addition, when the determination unit 932 determines that the brightness signal value of the second corresponding pixel corresponding to the target pixel in the second captured image is not a predetermined threshold value or more, the generation unit 933 outputs the brightness signal value of the target pixel to be generated in the output image as the brightness signal value of the first corresponding pixel corresponding to the target pixel in the first captured image.

The input unit 94 is configured by using a keyboard, a mouse, a touch panel, and the like. The input unit 94 accepts input of various information by the user's operation.

The memory 95 is configured by using a volatile memory, a non-volatile memory, a frame memory, and the like. The memory 95 stores various programs executed by the endoscope system 1 or various data used during processing. Note that the memory 95 may further include a memory card and the like that is detachable with respect to the control device 9.

The output unit 96 is configured by using a speaker, a printer, a display, and the like. The output unit 96 outputs various information about the endoscope system 1.

The control unit 97 comprehensively controls each unit constituting the endoscope system 1. The control unit 97 is configured by using a memory, and hardware such as a CPU.

Processing of Endoscope System

Figure 3:
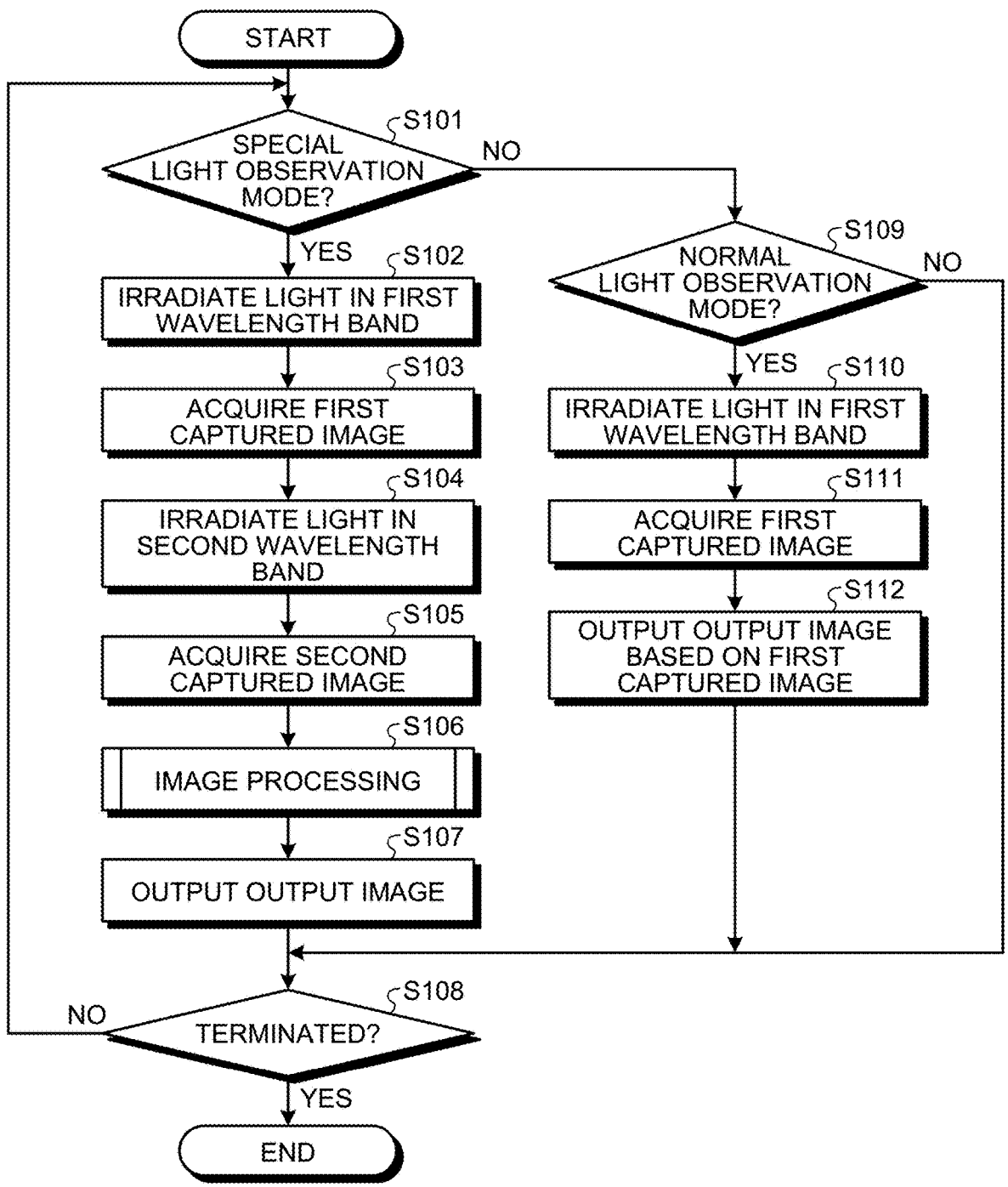
FIG. 3 is a flowchart illustrating an outline of processing executed by the endoscope system according to the first embodiment.

Next, processing executed by the endoscope system 1 will be described. FIG. 3 is a flowchart illustrating an outline of processing executed by the endoscope system 1.

As illustrated in FIG. 3, first, the control unit 97 determines whether or not the endoscope system 1 is in a special light observation mode based on observation mode information acquired from the memory 95 (step S101). When the control unit 97 determines that the endoscope system 1 is in the special light observation mode (step S101: Yes), the endoscope system 1 proceeds to step S102, which will be described later. On the other hand, when the control unit 97 determines that the endoscope system 1 is not in the special light observation mode (step S101: No), the endoscope system 1 proceeds to step S109, which will be described later.

Figure 4:
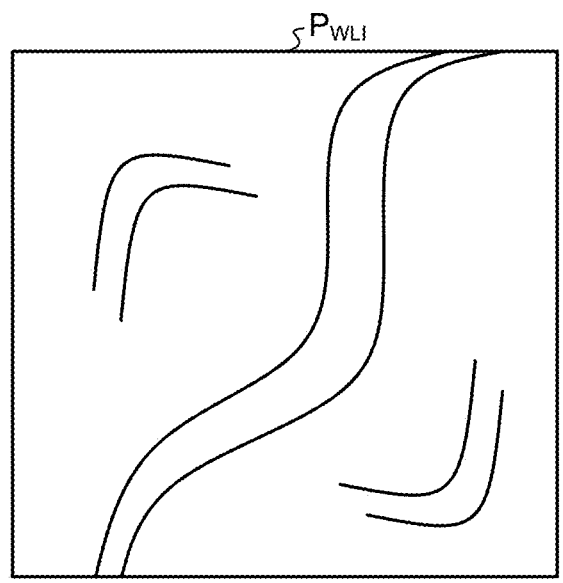
FIG. 4 is a diagram illustrating an example of a first captured image.

In step S102, the control unit 97 controls the light source control unit 33 to irradiate the first light source unit 31 with white light, which is light in the first wavelength band, toward the observation target of the subject. In this case, the imaging unit 502 receives reflected light reflected by the white light on the observation target via the lens unit 501 and generates the first captured image by performing photoelectric conversion. Specifically, the imaging unit 502 generates a first captured image $P_{WLI}$ (white light image) illustrated in FIG. 4.

Subsequently, the acquisition unit 931 acquires the first captured image from the imaging unit 502 via the communication module 503, the communication module 91, and the signal processing unit 92 (step S103).

Figure 5:
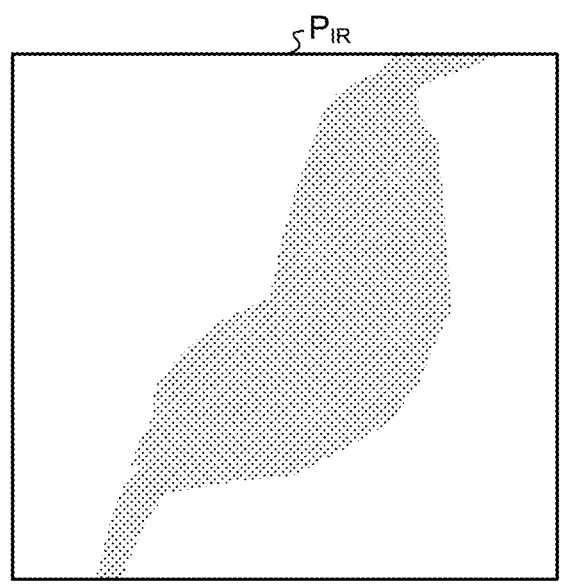
FIG. 5 is a diagram illustrating an example of a second captured image.

After that, the control unit 97 controls the light source control unit 33 to irradiate the second light source unit 32 with near-infrared light, which is special light, toward the observation target of the subject (step S104). In this case, the imaging unit 502 receives a fluorescence emitted by the excitation of the substance in the observation target via the lens unit 501, and generates the second captured image by performing photoelectric conversion. Specifically, a second captured image $P_{IR}$ (fluorescent image) illustrated in FIG. 5 is generated. Note that in FIG. 5, a fluorescence region is represented by dots.

Subsequently, the acquisition unit 931 acquires the second captured image from the imaging unit 502 via the communication module 503, the communication module 91, and the signal processing unit 92 (step S105).

Figure 6:
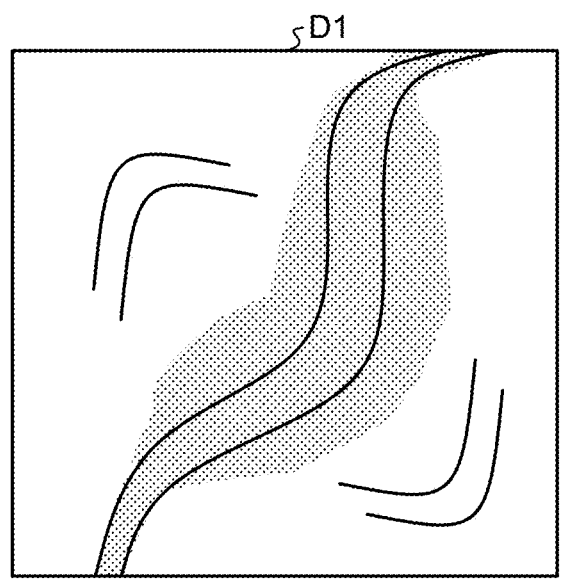
FIG. 6 is a diagram illustrating an example of a display image.

After that, the image processing unit 93 executes image processing of generating an output image by combining the first captured image and the second captured image with the corresponding pixels (step S106), and outputs the output image to the display device 7 (step S107). In this case, the display device 7 displays a display image Dl illustrated in FIG. 6. The display image Dl may clearly observe the details (for example, the structure and contour of the observation target) of the lesion portion included in the first captured image $P_{WLI}$ and the second captured image $P_{IR}$. Note that the details of the image processing will be described later.

Subsequently, when a termination signal for terminating the observation is input from the input unit 94 (step S108: Yes), the endoscope system 1 ends the processing. On the other hand, when the termination signal for terminating the observation is not input from the input unit 94 (step S108: No), the endoscope system 1 returns to the above-mentioned step S101.

In step S109, the control unit 97 determines whether or not the endoscope system 1 is in a normal light observation mode based on the observation mode information acquired from the memory 95. When the control unit 97 determines that the endoscope system 1 is in the normal light observation mode (step S109: Yes), the endoscope system 1 proceeds to step S110, which will be described later. On the other hand, when the control unit 97 determines that the endoscope system 1 is not in the normal light observation mode (step S109: No), the endoscope system 1 proceeds to step S108.

In step S110, the control unit 97 controls the light source control unit 33 to irradiate the first light source unit 31 with white light toward the observation target of the subject. In this case, the imaging unit 502 receives reflected light reflected by the white light on the observation target via the lens unit 501 and generates the first captured image by performing photoelectric conversion.

Subsequently, the acquisition unit 931 acquires the first captured image from the imaging unit 502 via the communication module 503, the communication module 91, and the signal processing unit 92 (step S111).

After that, the display device 7 displays a display image based on the first captured image subjected to normal image processing by the image processing unit 93 (step S112). After step S112, the endoscope system 1 proceeds to step S108.

Details of Image Processing

Figure 7:
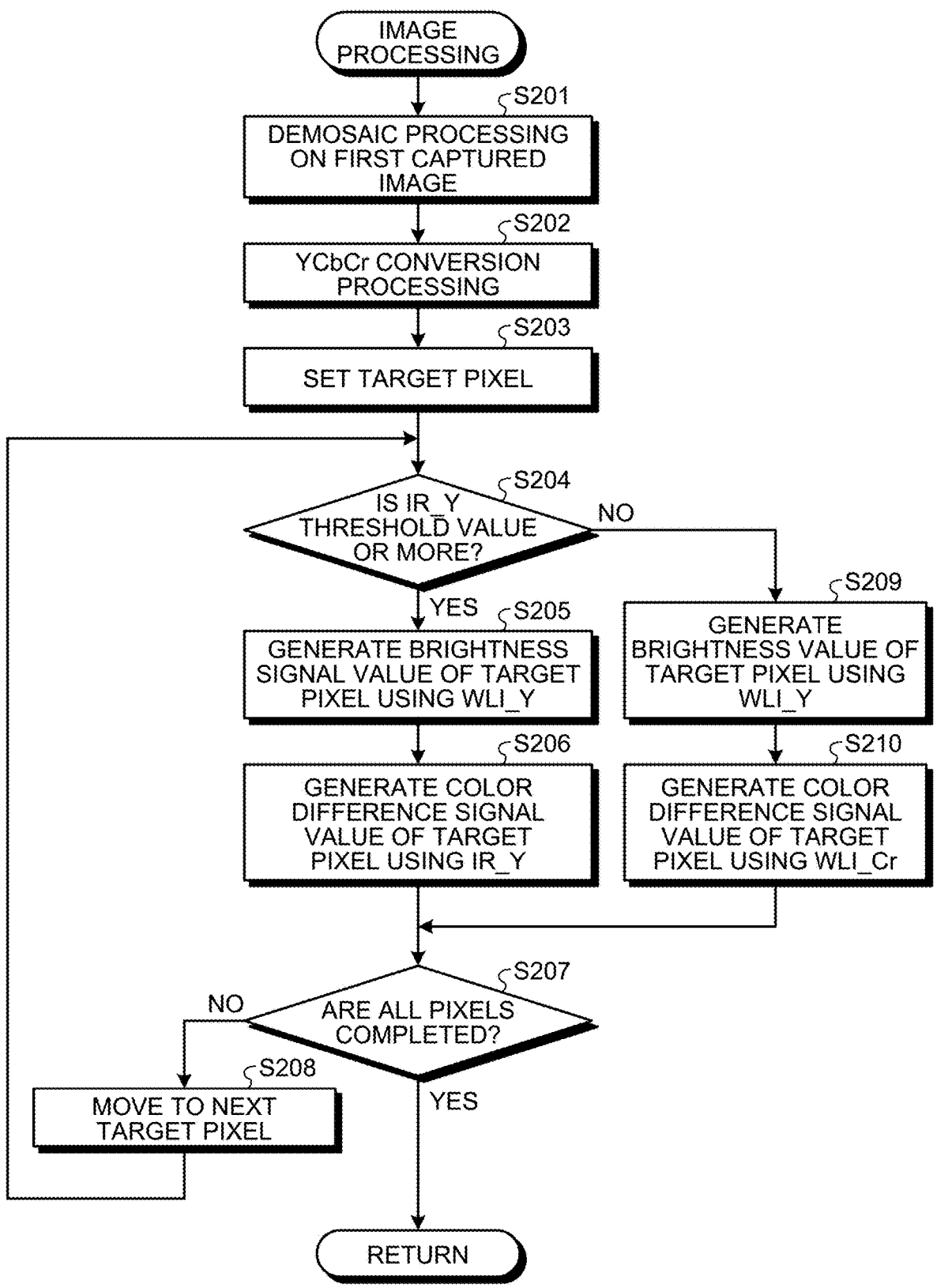
FIG. 7 is a flowchart illustrating an outline of image processing of FIG. 3.
Figure 8:
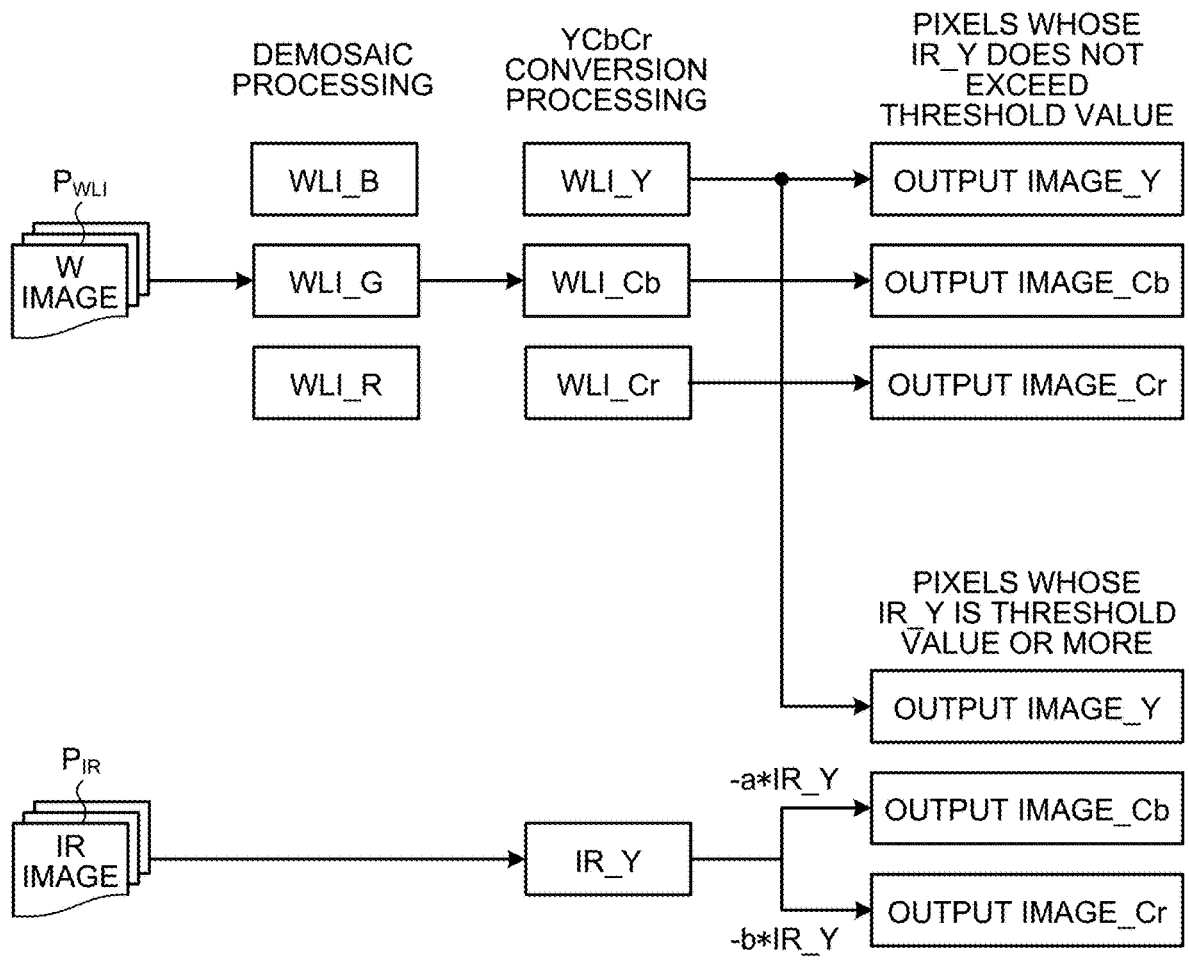
FIG. 8 is a diagram schematically illustrating an outline of image processing by an image processing unit according to the first embodiment.

Next, the details of the image processing described in step S106 of FIG. 3 will be described. FIG. 7 is a flowchart illustrating an outline of image processing. FIG. 8 is a diagram schematically illustrating an outline of image processing by the image processing unit 93.

As illustrated in FIG. 7, the generation unit 933 performs demosaic processing on the first captured image acquired by the acquisition unit 931 (step S201). Specifically, as illustrated in FIG. 8, the generation unit 933 performs the demosaic processing on the first captured image $P_{WLI}$ to generate a blue color image WLI_B, a green color image WLI_G, and a red color image WLI_R, respectively.

Subsequently, the generation unit 933 performs YCbCr conversion processing on each of the color image WLI_B, the color image WLI_G, the color image WLI_R, and the second captured image $P_{IR}$ (step S202). Specifically, as illustrated in FIG. 8, the generation unit 933 performs the YCbCr conversion processing on each of the color image WLI_B, the color image WLI_G, and the color image WLI_R to generate a brightness signal value WLI_Y, a color difference signal value WLI_Cb, and a color difference signal value WLI_Cr. Further, the generation unit 933 performs the YCbCr conversion process on the second captured image $P_{IR}$ to generate a brightness signal value IR_Y.

After that, the generation unit 933 sets a target pixel in the output image (step S203). Specifically, the generation unit 933 sets a pixel located on the left side in the uppermost stage of the output image as a first target pixel (attention pixel).

Subsequently, the determination unit 932 determines whether or not the brightness signal value IR_Y of the second captured image $P_{IR}$ corresponding to the target pixel is a threshold value or more (step S204). Here, the threshold value is a value of noise or more. When the determination unit 932 determines that the brightness signal value IR_Y of the second captured image IR corresponding to the target pixel is the threshold value or more (step S204: Yes), the image processing unit 93 proceeds to step S205, which will be described later. On the other hand, when it is determined that the brightness signal value IR_Y of the second captured image IR corresponding to the target pixel is not the threshold value or more (step S204: No), the image processing unit 93 proceeds to step S209, which will be described later.

In step S205, the generation unit 933 generates a brightness value of the target pixel in the output image by using the brightness signal value WLI_Y of the first captured image W1.

Subsequently, the generation unit 933 generates the Cb value and Cr value of the target pixel in the output image by using the brightness signal value IR_Y of the target pixel in the second captured image $P_{IR}$ (step S206). After step S206, the image processing unit 93 proceeds to step S207, which will be described later.

Figure 9:
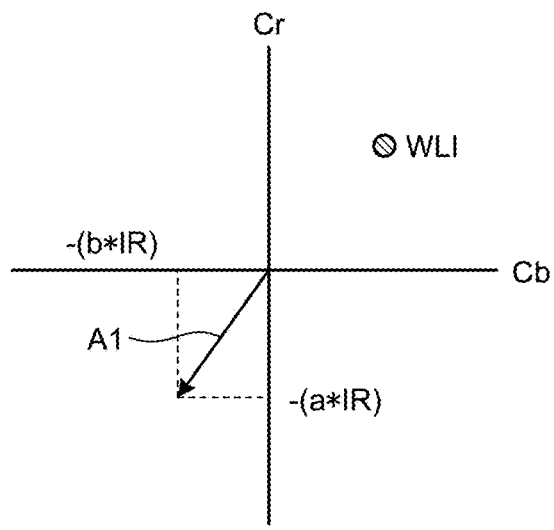
FIG. 9 is a diagram schematically illustrating an outline when a generation unit according to the first embodiment generates a Cb value and a Cr value of a target pixel in an output image.

FIG. 9 is a diagram schematically illustrating an outline when the generation unit 933 generates the Cb value and the Cr value of the target pixel in the output image.

As illustrated in FIG. 9, the generation unit 933 generates the Cb value and the Cr value of the target pixel in the output image by using the brightness signal value IR_Y of the target pixel in the second captured image $P_{IR}$. Specifically, as illustrated in FIG. 9, when a vector A1 is defined by two coefficients a and b for a pseudo color preset in a two-dimensional color space, the generation unit 933 generates the Cb value and Cr value of the target pixel in the output image by using a value obtained by multiplying the brightness signal value IR_Y of the target pixel in the second captured image $P_{IR}$ by the coefficient a, and a value obtained by multiplying the brightness signal value IR_Y of the target pixel in the second captured image $P_{IR}$ by the coefficient b. More specifically, the generation unit 933 generates the Cb value and the Cr value of the target pixel in the output image by the following equations (1) and (2).

$$Cb = -a * IR\_Y \qquad (1)$$

$$Cr = -b * IR\_Y \qquad (2)$$

However, the coefficients a and b satisfy the following conditions (1) and (2).

$$0 \le a \qquad \text{Condition (1)}$$

$$b \le 1 \qquad \text{Condition (2)}$$

In this way, when the vector A1 is defined by two coefficients a and b for the preset pseudo color in the two-dimensional color space represented by CbCr in the YCbCr color space, the generation unit 933 generates the Cb value and Cr value of the target pixel in the output image by using a value obtained by multiplying the brightness signal value IR_Y of the target pixel in the second captured image $P_{IR}$ by each of the coefficient a and the coefficient b. In this case, the two coefficients a and b are preferably set so that the preset pseudo color is green, which is an opposite color of the body color (for example, red) of the subject, but may be blue and cyan, for example. That is, in the first embodiment, a plurality of pseudo colors that may be selected by the user may be provided. In this case, the user such as a doctor selects a desired pseudo color from the plurality of pseudo colors via the input unit 94. At this time, the generation unit 933 sets the two coefficients a and b according to a selection signal for selecting one of the plurality of pseudo colors input from the input unit 94. As a result, the user may observe the fluorescence observation with a desired pseudo color.

Returning to FIG. 7, the description after step S207 is continued.

When all the pixels in the output image are completed in step S207 (step S207: Yes), the image processing unit 93 returns to a main routine of FIG. 3. On the other hand, when all the pixels in the output image are not completed (step S207: No), the image processing unit 93 proceeds to step S208.

In step S208, the generation unit 933 moves to a next target pixel in the output image. After step S208, the image processing unit 93 returns to step S204 described above.

In step S209, the generation unit 933 generates the brightness value of the target pixel in the output image by using the brightness signal value WLI_Y of the first captured image $P_{WLI}$.

Subsequently, the generation unit 933 generates the Cb value and the Cr value of the target pixel in the output image by using the color difference signal value WLI_Cb and the color difference signal value WLI_Cr in the first captured image $P_{WLI}$ (step S210). Specifically, as illustrated in FIG. 8, the generation unit 933 generates the Cb value and the Cr value of the target pixel in the output image by using the color difference signal value WLI_Cb and the color difference signal value WLI_Cr in the first captured image $P_{WLI}$. After step S210, the image processing unit 93 proceeds to step S207.

According to the first embodiment described above, since the image processing unit 93 outputs the brightness signal value of the target pixel to be generated in the output image as either the brightness signal value of the first corresponding pixel corresponding to the target pixel in the first captured image $P_{WLI}$ or the brightness signal value of the second corresponding pixel corresponding to the target pixel in the second captured image $P_{IR}$, and outputs the color difference signal value of the target pixel in the output image as the value generated by using the brightness signal value of the second corresponding pixel, an appropriately observable image is generated even when the normal white light and the special light observation image are combined.

In addition, according to the first embodiment, in the case where the vector A1 is defined by the two coefficients a and b for the preset pseudo color in the two-dimensional color space, since the image processing unit 93 outputs the Cb value and the Cr value, which are the color difference signal values of the target pixel in the output image, as the value generated by multiplying the brightness signal value of the second corresponding pixel corresponding to the target pixel in the second captured image $P_{IR}$ by the coefficient a, and the value generated by multiplying the brightness signal value of the second corresponding pixel corresponding to the target pixel in the second captured image $P_{IR}$ by the coefficient b, an appropriately observable image is generated even when the normal white light and the special light observation image are combined by simple processing.

In addition, according to the first embodiment, since the generation unit 933 outputs the brightness signal value of the target pixel to be generated in the output image as the brightness signal value of the second corresponding pixel corresponding to the target pixel in the second captured image $P_{IR}$ when the determination unit 932 determines that the brightness signal value of the second corresponding pixel corresponding to the target pixel in the second captured image $P_{IR}$ is the predetermined threshold value or more, and outputs the brightness signal value of the target pixel to be generated in the output image as the brightness signal value of the first corresponding pixel corresponding to the target pixel in the first captured image $P_{WLI}$ when the determination unit 932 determines that the brightness signal value of the second corresponding pixel corresponding to the target pixel in the second captured image $P_{IR}$ is not the predetermined threshold value or more, the influence of noise may be prevented.

In addition, according to the first embodiment, since the image processing unit 93 sets the two coefficients a and b according to the selection signal for selecting one of the plurality of pseudo colors input from the input unit 94, the fluorescence may be observed in the pseudo color desired by the user.

Note that in the first embodiment, the light in the first wavelength band and the light in the second wavelength band are alternately irradiated, but the present disclosure is not limited thereto, and for example, by providing an imaging unit capable of capturing the white light and an imaging unit provided with a cut filter on a light receiving surface for transmitting only the fluorescence, even when the first captured image $P_{WLI}$ and the second captured image $P_{IR}$ are acquired at the same time, or even when the normal white light and the special light observation image are combined by performing the image processing described above, an appropriately observable image may be generated.

Second Embodiment

Next, a second embodiment will be described. In the first embodiment described above, the IR observation is performed as the special light observation mode, but in the second embodiment, a PDD observation is performed as the special light observation mode. Hereinafter, a configuration of an endoscope system according to the second embodiment will be described. Note that the same components as those of the endoscope system 1 according to the first embodiment described above are designated by the same reference numerals, and detailed description thereof will be omitted.

Detailed Configuration of Light Source Device, Camera Head, and Control Device

Figure 10:
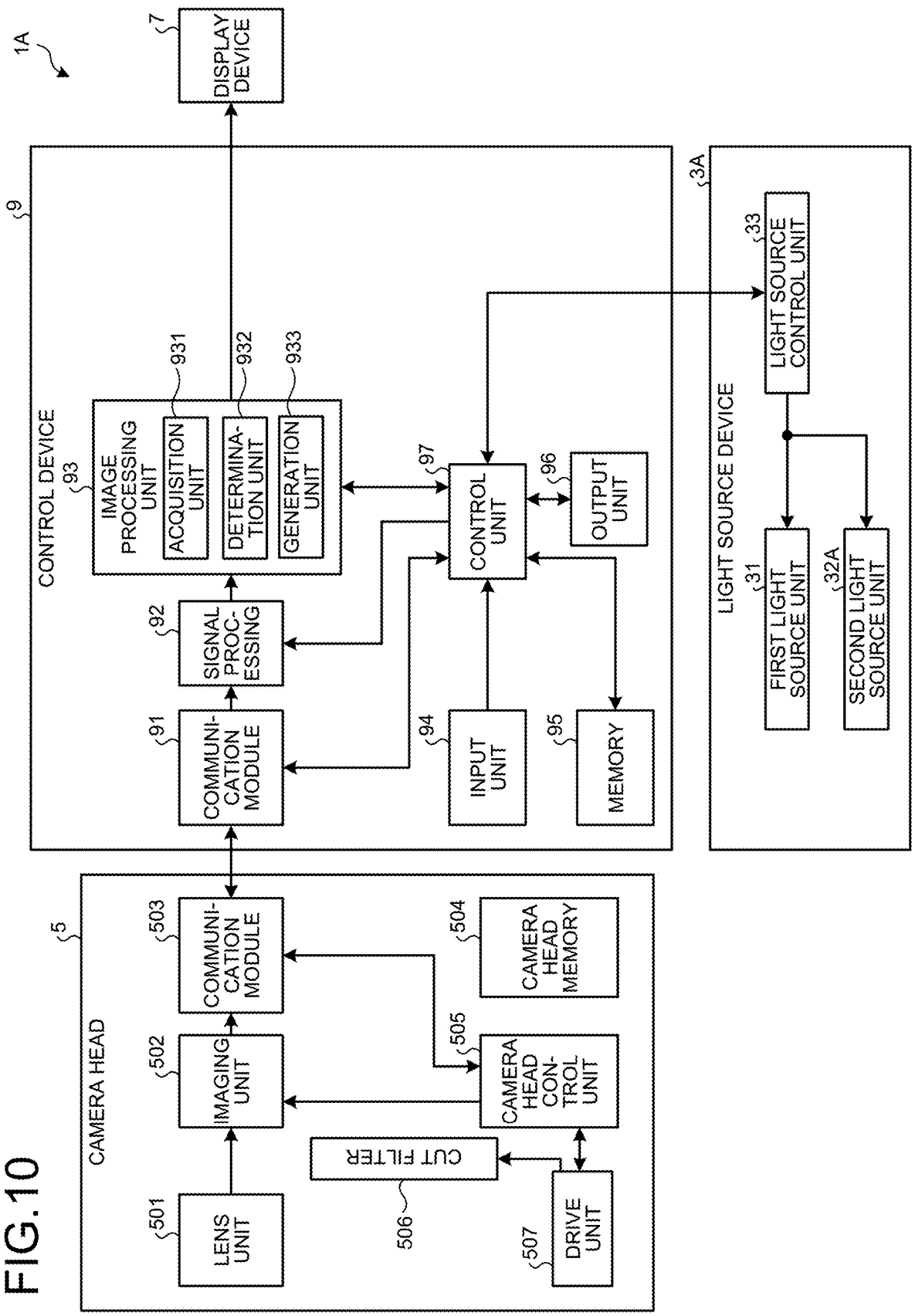
FIG. 10 is a block diagram illustrating a functional configuration of a light source device, a camera head, and a control device included in an endoscope system according to a second embodiment.

FIG. 10 is a block diagram illustrating a functional configuration of a light source device, a camera head, and a control device included in an endoscope system. The endoscope system 1A illustrated in FIG. 10 includes a light source device 3A and a camera head 5A in place of the light source device 3 and the camera head 5 of the endoscope system 1 according to the first embodiment described above. Note that in FIG. 10, for convenience of explanation, the insertion portion 2, the light guide 4, the first transmission cable 6, the second transmission cable 8, and the third transmission cable 10 are omitted.

Configuration of Light Source Device

First, a configuration of the light source device 3A will be described.

The light source device 3A includes a second light source unit 32A in place of the second light source unit 32 of the light source device 3 according to the first embodiment described above.

Under the control of the light source control unit 33, the second light source unit 32A pulse-emits excitation light, which is one of the special lights irradiated to the subject via the insertion portion 2. Here, the excitation light used in the PDD observation is, for example, blue visible light in a wavelength band of 375 nm to 445 nm (peak is 410 nm). In addition, an administration of a photosensitive substance such as 5-aminolevulinic acid (hereinafter referred to as "5-ALA") is performed on the observation target of the subject. Note that the user such as a doctor may have a subject such as a patient take a solution of 5-ALA. The 5-ALA is a natural amino acid originally contained in the living body of animals and plants. The 5-ALA is taken up into cells after administration into the body and biosynthesized into protoporphyrin in mitochondria. Then, in cancer cells, protoporphyrins are excessively accumulated. In addition, the protoporphyrins that are excessively accumulated in the cancer cells have photoactivity. Therefore, when excited by excitation light (for example, blue visible light in the wavelength band of 375 nm to 445 nm), the protoporphyrin emits fluorescence (for example, red fluorescence in the wavelength band of 600 nm to 740 nm). As described above, the PDD observation is an observation using photodynamic diagnosis, which is a cancer diagnostic method for fluorescing cancer cells using a light-sensitive substance. The second light source unit 32A is configured by using a semiconductor laser capable of irradiating excitation light that excites a substance (fluorescent substance) injected into the observation target of the subject, a filter that transmits only a predetermined wavelength band (for example, a wavelength band of 375 nm to 445 nm), and the like.

Configuration of Camera Head

Next, a configuration of the camera head 5A will be described.

The camera head 5A further includes a cut filter 506 and a drive unit 507, in addition to the configuration of the camera head 5 according to the first embodiment described above.

The cut filter 506 is detachably provided on an optical path of the lens unit 501 between the lens unit 501 and the imaging unit 502. The cut filter 506 is realized by using a band stop filter that cuts a specific wavelength band. Specifically, the cut filter 506 cuts light in the wavelength band (375 nm to 445 nm) of the excitation light that is irradiated by the second light source unit 32A and reflected by the observation target of the subject, and transmits light in the wavelength band of fluorescence (600 nm to 740 nm).

The drive unit 507 arranges the cut filter 506 on the optical path of the lens unit 501 under the control of the camera head control unit 505. The drive unit 507 is realized by using, for example, a stepping motor, a DC motor, or the like.

The endoscope system 1A configured in this way performs the same processing as in the first embodiment described above, and in the normal observation light mode, the cut filter 506 is retracted from the optical path of the lens unit 501. Further, in the special light observation mode, the endoscope system 1A retracts the cut filter 506 from the optical path of the lens unit 501 when the first light source unit 31 irradiates white light, and moves the cut filter 506 onto the optical path of the lens unit 501 when the second light source unit 32A irradiates excitation light. Then, the image processing unit 93 performs the same image processing as in the first embodiment described above. In this case, the user selects a pseudo color suitable for the PDD observation from a plurality of pseudo colors via the input unit 94. At this time, the generation unit 933 sets the two coefficients a and b according to a selection signal for selecting one of the plurality of pseudo colors input from the input unit 94. As a result, the user may observe the fluorescence observation with a desired pseudo color even in the PDD observation.

According to the second embodiment described above, an appropriately observable image may be generated even when the normal white light and the special light observation image are combined in the PDD observation.

Modified Example of Second Embodiment

Next, a modified example of the second embodiment described above will be described. The modified example of the second embodiment has a different configuration from the camera head 5A of the endoscope system 1A according to the second embodiment described above. Hereinafter, a camera head according to the modified example of the second embodiment will be described. Note that the same components as those of the endoscope system 1A according to the second embodiment described above are designated by the same reference numerals, and detailed description thereof will be omitted.

Configuration of Camera Head

Figure 11:
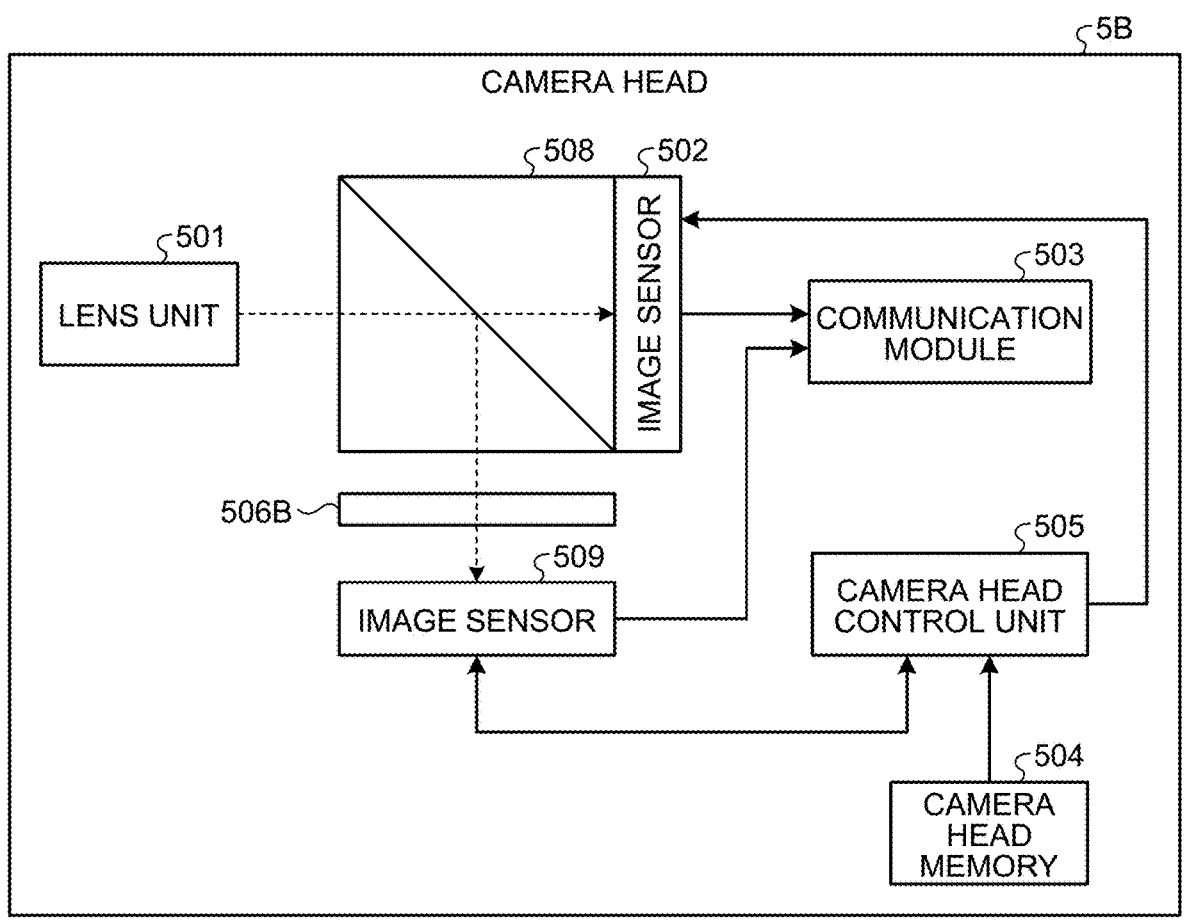
FIG. 11 is a block diagram illustrating a functional configuration of a camera head according to a modified example of the second embodiment.

FIG. 11 is a block diagram illustrating a functional configuration of a camera head according to a modified example of the second embodiment. A camera head 5B illustrated in FIG. 11 further includes a prism 508, a cut filter 506B, and an image sensor 509, in place of the cut filter 506 and the drive unit 507 of the camera head 5A according to the second embodiment described above.

The prism 508 disperses the subject image captured by the lens unit 501 onto the imaging surfaces of the imaging unit 502 and the image sensor 509.

The cut filter 506B cuts the light in the wavelength band (375 nm to 445 nm) of the excitation light reflected by the observation target of the subject included in the subject image incident from the prism 508, and also transmits the light in the wavelength band of fluorescence (600 nm to 740 nm).

Under the control of the camera head control unit 505, the image sensor 509 receives the light transmitted through the cut filter 506B and performs photoelectric conversion to generate a second captured image. The image sensor 509 transmits the second captured image to the communication module 503. The image sensor 509 is realized by using a CCD, a CMOS, and the like.

According to the modified example of the second embodiment described above, the first captured image and the second captured image may be acquired at the same time.

Third Embodiment

Next, a third embodiment will be described. In the first embodiment described above, the case where the present disclosure is applied to a rigid endoscope system using a rigid endoscope has been described, but in the third embodiment, the case where the present disclosure is applied to a flexible endoscope system using a flexible endoscope will be described. Note that the same components as those of the endoscope system 1 according to the first embodiment described above are designated by the same reference numerals, and detailed description thereof will be omitted.

Outline Configuration of Endoscope System

Figure 12:
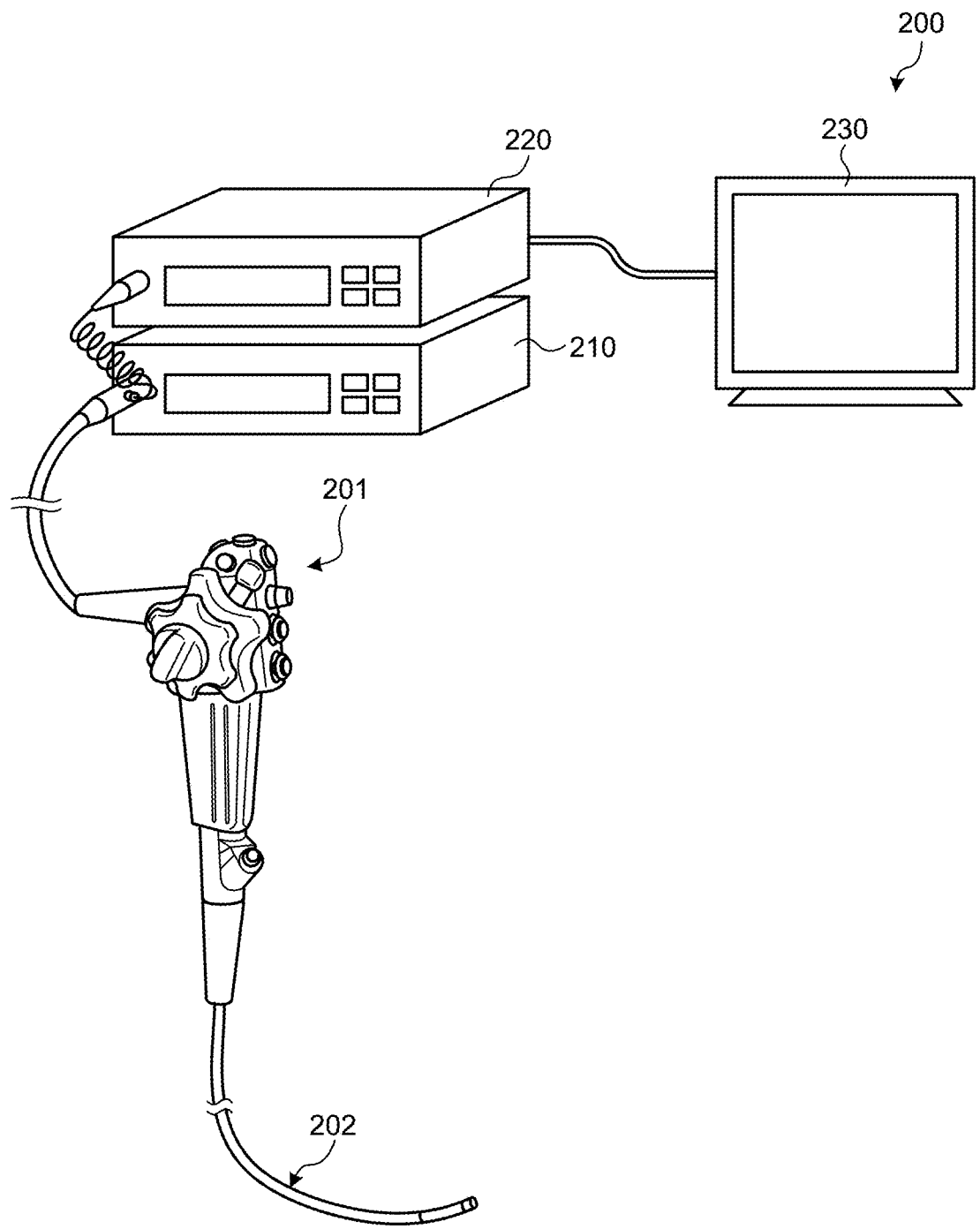
FIG. 12 is a diagram illustrating a schematic configuration of an endoscope system according to a third embodiment.

FIG. 12 is a diagram illustrating a schematic configuration of an endoscope system according to the third embodiment. An endoscope system 200 illustrated in FIG. 12 includes an endoscope 201 that captures an in-vivo image of an observed region by inserting an insertion portion 202 into a subject to generate image data, a light source device 210 that supplies white light or infrared light to the endoscope 201, a control device 220 that performs predetermined image processing on an imaging signal acquired by the endoscope 201 and comprehensively controls an operation of the entire endoscope system 200, and a display device 230 that displays an in-vivo image subjected to the image processing by the control device 220.

The endoscope 201 includes at least the lens unit 501 and the imaging unit 502 described above.

The light source device 210 includes at least the first light source unit 31, a second light source unit 32, and a light source control unit 33 described above.

The control device 220 includes at least the communication module 91, the signal processing unit 92, the image processing unit 93, the input unit 94, the memory 95, the output unit 96, and the control unit 97 described above.

According to the third embodiment described above, the same effect as that of the first embodiment described above may be obtained even with the flexible endoscope system 200.

Fourth Embodiment

Next, a fourth embodiment will be described. In the first to the third embodiments described above, the endoscope system was used, but in the fourth embodiment, a case where the present disclosure is applied to a surgical microscope system will be described. Note that the same components as those of the endoscope system 1 according to the first embodiment described above are designated by the same reference numerals, and detailed description thereof will be omitted.

Configuration of Surgical Microscope System

Figure 13:
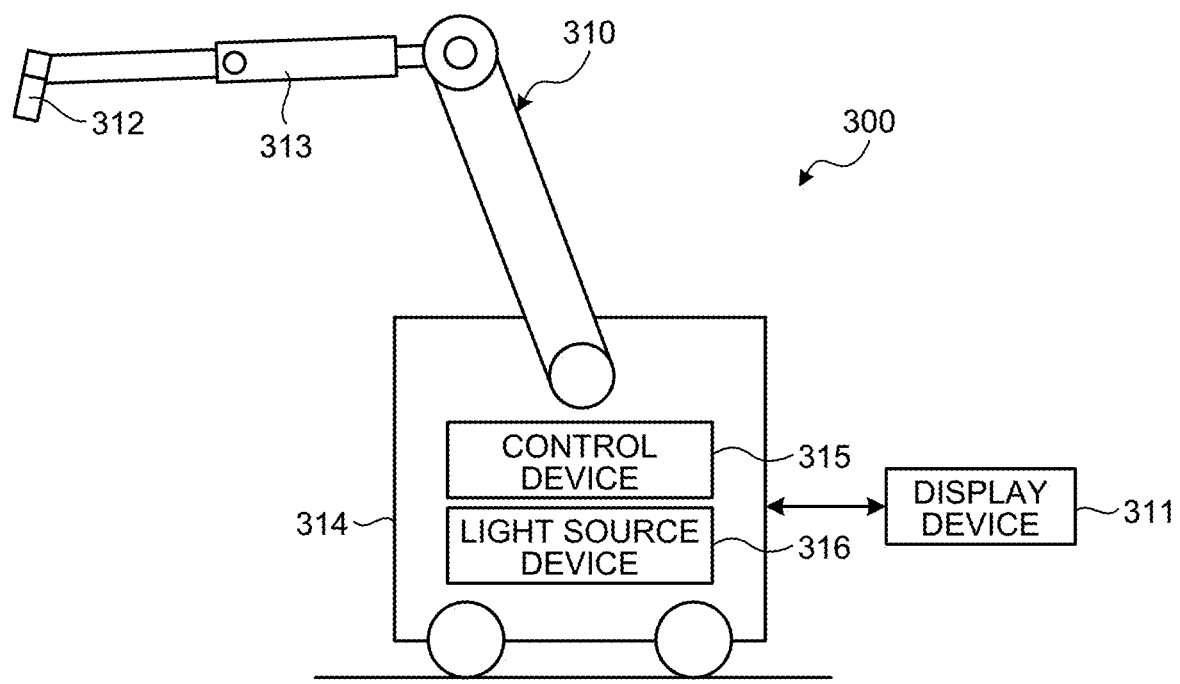
FIG. 13 is a diagram illustrating a schematic configuration of a surgical microscope system according to a fourth embodiment.

FIG. 13 is a diagram illustrating a schematic configuration of a surgical microscope system according to the fourth embodiment. A surgical microscope system 300 illustrated in FIG. 13 includes a microscope device 310, which is a medical imaging device acquired by capturing an image for observing a subject, and a display device 311 that displays an image captured by the microscope device 310. Note that it is also possible to integrally configure the display device 311 and the microscope device 310.

The microscope device 310 includes a microscope portion 312 that magnifies and captures a microscopic portion of the subject, a support portion 313 that includes an arm that is connected to a proximal end portion of the microscope portion 312 and that rotatably supports the microscope portion 312, and a base portion 314 that rotatably holds the proximal end portion of the support portion 313 and is movable on a floor surface. The base portion 314 includes a control device 315 that controls the operation of the surgical microscope system 300, and a light source device 316 that generates white light, special light (infrared light), and the like, which is irradiated from the microscope device 310 to the subject. Note that the control device 315 includes at least the communication module 91, the signal processing unit 92, the image processing unit 93, the input unit 94, the memory 95, the output unit 96, and the control unit 97 described above. In addition, the light source device 316 includes at least the first light source unit 31, the second light source unit 32, and the light source control unit 33 described above. In addition, the base portion 314 may not be movably provided on the floor surface, but may be fixed to a ceiling, a wall surface, and the like to support the support portion 313.

The microscope portion 312 has, for example, a columnar shape and has the lens unit 501 and imaging unit 502 therein. A switch that receives an input of an operation instruction of the microscope device 310 is provided on a side surface of the microscope portion 312. A cover glass (not illustrated) that protects the inside is provided on an opening surface at a lower end portion of the microscope portion 312.

In the surgical microscope system 300 configured in this way, a user such as an operator may move the microscope portion 312, perform a zoom operation, or switch illumination light while grasping the microscope portion 312 and operating various switches. The shape of the microscope portion 312 is preferably a shape that is elongated in an observation direction so that the user may easily grasp and change a viewing direction. Therefore, the shape of the microscope portion 312 may be shaped other than a cylindrical shape, and may be, for example, a polygonal pillar shape.

According to the fourth embodiment described above, the same effect as that of the first embodiment may be obtained in the surgical microscope system 300.

Other Embodiments

Variations may be formed by appropriately combining a plurality of components disclosed in the medical observation system according to the first to fourth embodiments described above. For example, some components may be deleted from all the components described in the medical observation system according to the first to fourth embodiments described above. Further, the components described in the medical observation system according to the first to fourth embodiments described above may be appropriately combined.

In addition, in the second embodiment described above, the number of camera heads is one, but is not limited thereto, and for example, two camera heads may be used, and one camera head may generate a first captured image and the other camera head may generate a second captured image. In this case, the cut filter used in the second embodiment or the modified example of the second embodiment may be provided between the lens unit and the image sensor on the other camera head. As a result, the first captured image (white light image) and the second captured image (special light image) may be acquired at the same time.

In addition, in the second embodiment described above, the cut filter is provided, but the present disclosure is not limited thereto, and for example, a die clock mirror, and the like may be used.

In addition, in the first to fourth embodiments described above, the infrared light is described as the special light emitted by the second light source unit 32, but the present disclosure is not limited thereto, and for example, light (wavelength band 390 to 470 nm+wavelength band 540 to 560 nm) used for auto fluorescence imaging (AFI) observation for observing auto fluorescence from a fluorescent substance such as collagen may also be applied.

In addition, in the medical observation system according to the first to fourth embodiments, the above-mentioned "unit" may be read as "means" or "circuit". For example, the control unit may be read as a control means or a control circuit.

In addition, the programs to be executed by the medical observation system according to the first to fourth embodiments are recorded and provided on a computer-readable recording medium such as a CD-ROM, a flexible disk (FD), a CD-R, a digital versatile disk (DVD), a USB medium, or a flash memory as file data in an installable format or an executable format.

In addition, the programs to be executed by the medical observation system according to the first to fourth embodiments may be stored on a computer connected to a network such as the Internet and provided by downloading via the network.

Note that in the explanation of the timing chart in the present specification, the context of the processing between the timings is clarified by using expressions such as "first", "after", and "continued", but the order of processing to carry out the present disclosure is not uniquely defined by those expressions. That is, the order of processing in the timing chart described in the present specification may be changed within a consistent range.

Although some of the embodiments of the present application have been described in detail with reference to the drawings, these are examples, and it is possible to carry out the present disclosure in other forms in which various modifications and improvements have been made based on the knowledge of those skilled in the art, including the aspects described in the column of the present disclosure.

Note that the present technique may also have the following configurations.

(1) A medical image processing device including
an image processor configured to:
generate an output image by combining a first captured image obtained by capturing light from an observation target irradiated with light in a first wavelength band and a second captured image obtained by capturing fluorescence from the observation target irradiated with excitation light, with corresponding pixels, the first captured image being an observation target that emits the fluorescence when irradiated with the excitation light in a second wavelength band that is different from the light in the first wavelength band and being input from the outside, and the second captured image being input from the outside;
output a brightness signal value of a target pixel to be generated in the output image, as either a brightness signal value of a first corresponding pixel corresponding to the target pixel in the first captured image or a brightness signal value of a second corresponding pixel corresponding to the target pixel in the second captured image; and
output a color difference signal value of the target pixel in the output image as a value generated by using the brightness signal value of the second corresponding pixel.

(2) The medical image processing device according to (1), wherein
when a vector is defined by two coefficients a and b for a preset pseudo color in a two-dimensional color space, the image processor is configured to output a Cb value and a Cr value, which are color difference signal values of the target pixel in the output image, as a value generated by multiplying the brightness signal value of the second corresponding pixel corresponding to the target pixel in the second captured image by the coefficient a, and a value generated by multiplying the brightness signal value of the second corresponding pixel corresponding to the target pixel in the second captured image by the coefficient b, and
the coefficient a and the coefficient b satisfy the following conditions 1 and 2.

$$0 \le a \qquad \text{Condition (1)}$$

$$b \le 1 \qquad \text{Condition (2)}$$

(3) The medical image processing device according to (2), wherein the image processor is configured to:
determine whether or not the brightness signal value of the second corresponding pixel corresponding to the target pixel in the second captured image is a predetermined threshold value or more,
output the brightness signal value of the target pixel to be generated in the output image as the brightness signal value of the second corresponding pixel corresponding to the target pixel in the second captured image, when the brightness signal value of the second corresponding pixel corresponding to the target pixel in the second captured image is the predetermined threshold value or more, and
output the brightness signal value of the target pixel to be generated in the output image as the brightness signal value of the first corresponding pixel corresponding to the target pixel in the first captured image, when the brightness signal value of the second corresponding pixel corresponding to the target pixel in the second captured image is not the predetermined threshold value or more.

(4) The medical image processing device according to (2) or (3), wherein
the light in the first wavelength band is white light, and
the excitation light has a wavelength band of either 750 nm to 810 nm or 375 nm to 445 nm.

(5) The medical image processing device according to (2) or (3), wherein
the light in the first wavelength band is white light, and
the excitation light is light in a wavelength band in which the observation target generates auto fluorescence.

(6) The medical image processing device according to any one of (2) to (5), wherein
a plurality of pseudo colors are selected, and
the image processor is configured to set the two coefficients a and b based on a selection signal for selecting one of the plurality of pseudo colors input from the outside.

(7) The medical image processing device according to any one of (2) to (6), wherein the pseudo color is set to an opposite color opposite to the observation target.

(8) A medical observation system including:
a light source configured to emit either light in a first wavelength band or excitation light in a second wavelength band different from the light in the first wavelength band;
an imager configured to generate a first captured image by capturing light from an observation target irradiated with the light in the first wavelength band and generates a second captured image by capturing the fluorescence from the observation target irradiated with the excitation light, the first captured image being the observation target that emits the fluorescence when irradiated with the excitation light; and
an image processor configured to
generate an output image by combining the first captured image and the second captured image with corresponding pixels, output a brightness signal value of a target pixel to be generated in the output image, as either a brightness signal value of a first corresponding pixel corresponding to the target pixel in the first captured image or a brightness signal value of a second corresponding pixel corresponding to the target pixel in the second captured image, and output a color difference signal value of the target pixel in the output image as a value generated by using the brightness signal value of the second corresponding pixel.

(9) An image processing method including:

acquiring a first captured image obtained by capturing light from an observation target irradiated with light in a first wavelength band and a second captured image obtained by capturing fluorescence from the observation target irradiated with excitation light, the first captured image being an observation target that emits the fluorescence when irradiated with the excitation light in a second wavelength band that is different from the light in the first wavelength band;

when an output image is generated by combining the first captured image and the second captured image with corresponding pixels, outputting a brightness signal value of a target pixel to be generated in the output image, as either a brightness signal value of a first corresponding pixel corresponding to the target pixel in the first captured image or a brightness signal value of a second corresponding pixel corresponding to the target pixel in the second captured image; and outputting a color difference signal value of the target pixel in the output image as a value generated by using the brightness signal value of the second corresponding pixel.

According to the present disclosure, even when the normal white light and the special light observation image are combined, an effect that an appropriately observable image may be generated may be obtained.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical image processing device comprising an image processor configured to:

generate an output image by combining a first captured image obtained by capturing light from an observation target irradiated with light in a first wavelength band and a second captured image obtained by capturing fluorescence from the observation target irradiated with excitation light, with corresponding pixels, the second captured image being an image of the observation target that emits the fluorescence when irradiated with the excitation light in a second wavelength band that is different from the light in the first wavelength band;

output a brightness signal value of a target pixel to be generated in the output image, as either a brightness signal value of a first corresponding pixel corresponding to the target pixel in the first captured image or a brightness signal value of a second corresponding pixel corresponding to the target pixel in the second captured image; and output a color difference signal value of the target pixel in the output image as a value generated by using the brightness signal value of the second corresponding pixel, wherein when a vector is defined by two coefficients a and b for a preset pseudo color in a two-dimensional color space, the image processor is configured to output a Cb value and a Cr value, which are color difference signal values of the target pixel in the output image, as a value generated by multiplying the brightness signal value of the second corresponding pixel corresponding to the target pixel in the second captured image by the coefficient a, and a value generated by multiplying the brightness signal value of the second corresponding pixel corresponding to the target pixel in the second captured image by the coefficient b, and the coefficient a and the coefficient b satisfy the following conditions 1 and 2, $$0 \leq a \qquad \text{Condition (1)}$$

$$b \leq 1 \qquad \text{Condition (2).}$$

2. The medical image processing device according to claim 1, wherein the image processor is configured to:

determine whether or not the brightness signal value of the second corresponding pixel corresponding to the target pixel in the second captured image is a predetermined threshold value or more, output the brightness signal value of the target pixel to be generated in the output image as the brightness signal value of the second corresponding pixel corresponding to the target pixel in the second captured image, when the brightness signal value of the second corresponding pixel corresponding to the target pixel in the second captured image is the predetermined threshold value or more, and output the brightness signal value of the target pixel to be generated in the output image as the brightness signal value of the first corresponding pixel corresponding to the target pixel in the first captured image, when the brightness signal value of the second corresponding pixel corresponding to the target pixel in the second captured image is not the predetermined threshold value or more.

3. The medical image processing device according to claim 1, wherein the light in the first wavelength band is white light, and the excitation light has a wavelength band of either 750 nm to 810 nm or 375 nm to 445 nm.

4. The medical image processing device according to claim 1, wherein the light in the first wavelength band is white light, and the excitation light is light in a wavelength band in which the observation target generates auto fluorescence.

5. The medical image processing device according to claim 1, wherein a plurality of pseudo colors is selected, and the image processor is configured to set the two coefficients a and b based on a selection signal for selecting one of the plurality of pseudo colors.

6. The medical image processing device according to claim 1, wherein the pseudo color is set to an opposite color opposite to the observation target.

7. The medical image processing device according to claim 2, wherein the light in the first wavelength band is white light, and the excitation light has a wavelength band of either 750 nm to 810 nm or 375 nm to 445 nm.

8. The medical image processing device according to claim 2, wherein the light in the first wavelength band is white light, and
the excitation light is light in a wavelength band in which
the observation target generates auto fluorescence.

9. The medical image processing device according to claim 2, wherein
a plurality of pseudo colors are selected, and
the image processor is configured to set the two coefficients a and b based on a selection signal for selecting one of the plurality of pseudo colors.

10. The medical image processing device according to claim 3, wherein
a plurality of pseudo colors are is selected, and
the image processor is configured to set the two coefficients a and b based on a selection signal for selecting one of the plurality of pseudo colors.

11. The medical image processing device according to claim 2, wherein the pseudo color is set to an opposite color opposite to the observation target.

12. The medical image processing device according to claim 3, wherein the pseudo color is set to an opposite color opposite to the observation target.

13. The medical image processing device according to claim 5, wherein the pseudo color is set to an opposite color opposite to the observation target.

14. A medical observation system comprising:
a light source configured to emit either light in a first wavelength band or excitation light in a second wavelength band different from the light in the first wavelength band;
an imager configured to generate a first captured image by capturing light from an observation target irradiated with the light in the first wavelength band and generates a second captured image by capturing the fluorescence from the observation target irradiated with the excitation light, the second captured image being an image of the observation target that emits the fluorescence when irradiated with the excitation light; and
an image processor configured to
generate an output image by combining the first captured image and the second captured image with corresponding pixels,
output a brightness signal value of a target pixel to be generated in the output image, as either a brightness signal value of a first corresponding pixel corresponding to the target pixel in the first captured image or a brightness signal value of a second corresponding pixel corresponding to the target pixel in the second captured image, and
output a color difference signal value of the target pixel in the output image as a value generated by using the brightness signal value of the second corresponding pixel, wherein
when a vector is defined by two coefficients a and b for a preset pseudo color in a two-dimensional color space, the image processor is configured to output a Cb value and a Cr value, which are color difference signal values of the target pixel in the output image, as a value generated by multiplying the brightness signal value of the second corresponding pixel corresponding to the target pixel in the second captured image by the coefficient a, and a value generated by multiplying the brightness signal value of the second corresponding pixel corresponding to the target pixel in the second captured image by the coefficient b, and
the coefficient a and the coefficient b satisfy the following conditions 1 and 2, $0 \leq a$      Condition (1)

$b \leq 1$      Condition (2).

15. An image processing method comprising:
acquiring a first captured image obtained by capturing light from an observation target irradiated with light in a first wavelength band and a second captured image obtained by capturing fluorescence from the observation target irradiated with excitation light, the second captured image being an image of the observation target that emits the fluorescence when irradiated with the excitation light in a second wavelength band that is different from the light in the first wavelength band;
when an output image is generated by combining the first captured image and the second captured image with corresponding pixels, outputting a brightness signal value of a target pixel to be generated in the output image, as either a brightness signal value of a first corresponding pixel corresponding to the target pixel in the first captured image or a brightness signal value of a second corresponding pixel corresponding to the target pixel in the second captured image; and
outputting a color difference signal value of the target pixel in the output image as a value generated by using the brightness signal value of the second corresponding pixel, wherein
when a vector is defined by two coefficients a and b for a preset pseudo color in a two-dimensional color space, the image processor is configured to output a Cb value and a Cr value, which are color difference signal values of the target pixel in the output image, as a value generated by multiplying the brightness signal value of the second corresponding pixel corresponding to the target pixel in the second captured image by the coefficient a, and a value generated by multiplying the brightness signal value of the second corresponding pixel corresponding to the target pixel in the second captured image by the coefficient b, and
the coefficient a and the coefficient b satisfy the following conditions 1 and 2, $0 \leq a$      Condition (1)

$b \leq 1$      Condition (2).

* * * * *